United States Patent
Kaneko et al.

(10) Patent No.: US 7,313,968 B2
(45) Date of Patent: Jan. 1, 2008

(54) PRESSURE DETECTOR AND PRESSURE DETECTING METHOD

(75) Inventors: Mitsuru Kaneko, Hiroshima (JP);
Noriaki Nakagawa, Hiroshima (JP);
Tadashi Okiyama, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 10/543,634

(22) PCT Filed: Jan. 30, 2003

(86) PCT No.: PCT/JP03/00906

§ 371 (c)(1),
(2), (4) Date: Aug. 15, 2006

(87) PCT Pub. No.: WO2004/081508

PCT Pub. Date: Sep. 23, 2004

(65) Prior Publication Data

US 2006/0278001 A1     Dec. 14, 2006

(51) Int. Cl.
*G01L 7/00*     (2006.01)
(52) U.S. Cl. .......................................... 73/756; 73/706
(58) Field of Classification Search ................. 73/700, 73/706, 756
See application file for complete search history.

(56) References Cited

U.S. PATENT DOCUMENTS

| | | | | |
|---|---|---|---|---|
| 5,957,121 A | * | 9/1999 | Suzuki et al. | 126/247 |
| 5,966,892 A | * | 10/1999 | Platt | 52/712 |
| 6,280,406 B1 | | 8/2001 | Dolecek et al. | |
| 6,371,227 B2 | * | 4/2002 | Bartlett | 180/24.02 |
| 6,668,659 B2 | * | 12/2003 | Morikawa et al. | 73/729.1 |

FOREIGN PATENT DOCUMENTS

| JP | 4-1948 Y2 | 1/1988 |
|---|---|---|
| JP | 3-49851 Y2 | 5/1991 |
| JP | 08-166301 | 6/1996 |
| JP | 2002-513321 A | 5/2002 |
| JP | 2002-233570 A | 8/2002 |
| JP | 2002-257656 A | 9/2002 |

* cited by examiner

*Primary Examiner*—Andre J. Allen
(74) *Attorney, Agent, or Firm*—Wolf, Greenfield & Sacks, P.C.

(57) ABSTRACT

A pressure detector having a pipe inner pressure receiving opening section comprising a fluid passage for transporting fluid and a diaphragm hermetically sealing an opening made in one side face of the fluid passage, and a pressure detecting section coupled with the pipe inner pressure receiving opening section through the diaphragm and detecting physical variation of the diaphragm, characterized in that the diaphragm is provided loosely at the opening, and the pressure detecting section comprises at least a pressure detector, a load transmitting means having one end connected with the diaphragm and the other end touching the pressure detector, and means for loading the pressure detector. Since a fluid being measured is not exposed directly to air, possibility of clogging the circuit with a blood clot can be reduced; and since a stress load on the diaphragm is reduced, irreversible creep deformation of the diaphragm can be prevented; thereby allowing the pressure detector to perform continuous measurement stably with high accuracy for a long time.

11 Claims, 2 Drawing Sheets

● Pressure measurements using a conventional drip chamber
○ Pressure measurements using the pressure detecting device of the present invention

PRESSURE DETECTOR AND PRESSURE DETECTING METHOD

TECHNICAL FIELD

The present invention in its purpose relates to a pressure detecting device which enables the construction of a system for continuously measuring in-pipe fluid pressure without exposing the fluid to the air and a pressure detecting method using the same pressure detecting device, and particularly to a pressure detecting device and pressure detecting method for measuring the in-pipe fluid pressure in an extra corporeal circulation line.

BACKGROUND ART

In a blood extra corporeal circulation therapy using a blood line, a continuous monitoring of the pressure in the blood line is of necessity as an alerting system against line blockage. A prevailing method for such monitoring is a method to monitor the pressure via an air layer using a drip chamber as a pressure receiving aperture part in order to avoid a blood counter flow toward the pressure measuring part and to remove air in the blood line. However, in such a method, blood coagulation is likely to occur due to the activation of coagulation factors at the interface between the air and blood in the drip chamber, resulting in a major cause of line blockage.

In particular, since a continuous blood purification method (CHDF, CHF, CHD), which involves a low flow rate of blood compared to general dialyses, is continuously operated for more than about 24 hours and is often used for patients with hemorrhagic lesion to whom administration of blood anticoagulant is undesirable, coagulation factors tend to be activated thereby causing a condition in which blood coagulation at the interface between blood and the air is likely to occur. Although the continuous blood purification is constantly controlled for nearly 24 hours mainly in an ICU (Intensive Care Unit), constant monitoring of the inner pressure of the circulating line is still important and is commonly performed. Nevertheless, there is constant danger of blood coagulation due to the contact with the air in the drip chamber. In view of these situations, conventionally, non-air-contact measurement techniques have been contrived as a method of measuring the pressure in an extra corporeal circulation blood line. JP,Y2, 4-1948 discloses a method of monitoring fluid pressure, in which a diaphragm for separating the air from blood was introduced into a drip chamber as a means for preventing the contact between the air and blood, and the pressure fluctuations of the air layer were monitored through the diaphragm. However, in this method, a problem existed in that when the chamber becomes a normal pressure for some reason, the diaphragm becomes an excessively stretched state disabling the pressure measurement thereafter.

On the other hand, there has been contrived a method, which is also a diaphragm method, but in which pressure is measured by placing a load cell into a direct and close contact with a diaphragm, instead of measuring pressure through an air layer. JP,A, 8-166301 discloses a method of measuring the inner pressure of a circulating line by using a pillow in an extra corporeal circulation line for similar purpose with a diaphragm and by placing a load cell in contact with the pillow. According to the aforementioned publication, it is made possible to accurately measure the pressure with a load cell by placing a holder cover which can maintain a predetermined space with respect to a pressure transfer plate as the means to prevent the changes in the contact area between a pillow diaphragm and the aforementioned plate. However, to detect negative pressure successfully, the pillow diaphragm is constantly applied with stress; and therefore the pillow diaphragm would deform when used for a long period of time thereby suffering a shift in zero point and degradation in pressure sensitivity. Further, in this method, since a polymer membrane is used as the material of the diaphragm, a creep deformation, which is characteristic of polymer materials, may occur, and therefore, this method is not suitable for measuring the pressure in a circulating line in a continuous and stable manner for a long period of time.

DISCLOSURE OF THE INVENTION

In view of above described situations, it is an object of the present invention to provide a pressure detecting device which employs a diaphragm/load cell scheme as the method of measuring the fluid pressure in a circulating line, in which the fluid to be measured is not directly exposed to air and the correction of the creep deformation of the diaphragm during measurement is possible, and which enables a continuous measurement of positive and negative pressures in the line in a stable and accurate manner for a long period of time, and also to provide a pressure detecting method by use of the aforementioned pressure detecting device.

Thus, in order to solve the above described problems, the pressure detecting device according to the present invention is a pressure detecting device for in-pipe fluid flow, having: an in-pipe pressure receiving aperture part comprising a fluid passage for transporting fluid and a diaphragm hermetically sealing an opening part made in one side of the fluid passage; and a pressure detecting part coupled with the in-pipe pressure receiving aperture part through the diaphragm and adapted to detect physical variation of the diaphragm, characterized in that the diaphragm is loosely mounted at the opening part, and the pressure detecting part at least comprises a pressure detecting element, a load transmitting means having one end connected with the diaphragm and the other end in contact with the pressure detecting element, and a load applying means for applying a load on the pressure detecting element.

Further, as used herein for the pressure detecting device according to the present invention, the term "loosely mounted" means that when placing a membrane-type object on the peripheral edge of an opening part of an object a membrane is mounted in a stretched but in a slackened state, differing from "stretchedly mounted" which means that a membrane is mounted in a stretched state.

The extent of the looseness in mounting the aforementioned diaphragm may be such that neither the passage of fluid nor the movement of the load transfer means connected to the diaphragm is hindered. Further, since this membrane needs to be loosely mounted at the in-pipe pressure receiving aperture part, it is preferable to use a membrane obtained by heat treating a planar membrane to make it deform into a suitable shape for loose mounting.

The pressure detecting device of the present invention can transfer the physical variation of a diaphragm generated in response to the fluctuations of fluid pressure to a pressure detecting element through a load transfer means without exposing the fluid to be measured to the air, and can measure the load by use of the pressure detecting element, thus making it possible to prevent blood coagulation due to air exposure and reduce the possibility of resulting blockage in the circulation line.

Further, since the aforementioned diaphragm is loosely mounted, that is mounted in a slackened state, to the opening part of the in-pipe pressure receiving aperture part as mentioned above, and the load transfer means connected to the diaphragm is applied with a pre-load toward the pressure detecting element by the load applying means, it is made possible to reduce the load onto the diaphragm and to prevent a creep deformation of the diaphragm thereby allowing a continuous blood pressure measurement at a high accuracy for a long period of time. As the result, it is not only made possible to perform safe operation of an extra corporeal blood circulation line, but also to facilitate the monitoring during the execution of extra corporeal circulation.

Further, the pressure detecting device of the present invention has achieved above described object even at a higher level by adopting the following configurations (1) to (9) in addition to the above described features.

(1) the load transfer means is connected to the diaphragm via a guide, preferably the load transfer means is connected to the diaphragm via a guide in a state in which the guide and the diaphragm are bonded together, (2) the aforementioned load transfer means and the aforementioned guide are connected through an engaging means provided on each of them, (3) the connection between the aforementioned load transfer means and the aforementioned guide is based on magnetic force, (4) the load transfer means is an elastic body, (5) the aforementioned elastic body is a coiled spring, (6) the aforementioned load applying means is based on a magnet, (7) the load applying means of (6) is based on an electromagnet, (8) the entire body of the aforementioned pressure detecting element is configured to be a hollow housing within which the load transfer means slides so that the load transfer means can vertically move with respect to the aforementioned device body, and (9) a positioning means is provided both at the in-pipe pressure receiving aperture part and the pressure detecting part so that the in-pipe pressure receiving aperture part and the pressure detecting part are detachably connected.

Further, as being used in this specification relating to the pressure detecting device or a pressure detecting method using the aforementioned pressure detecting device, terms "negative pressure" and "positive pressure" are defined such that a "negative pressure" is a state of lowered pressure and a "positive pressure" is a state of increased pressure with reference to the pressure in the fluid passage at the start of pressure detection.

The pressure detecting device of the present invention will be described in detail with reference to accompanying drawings. First, a general configuration of the pressure detecting device of the present invention will be described with reference to FIG. 1.

The pressure detecting device consists of a pressure detecting part A and an in-pipe pressure receiving aperture part B. The pressure detecting part A consists of: a housing 2 having a hollow part; a pressure detecting element 1 provided in the hollow part of the housing 2 at its distal end with respect to the in-pipe pressure receiving aperture part B; a load transfer means 3 having one end thereof in contact with the pressure detecting element 1 and the other end connected with the diaphragm 8 of the in-pipe pressure receiving aperture part B via a guide 10, and provided to be slidable in the hollow part of the housing 2; and a load transfer means 4 arranged to apply a load on the load applying means 3 toward the pressure detecting element 1 (X direction in the figure).

On the other hand, the in-pipe pressure receiving aperture part B consists of: a base 5 having a fluid passage 7; an opening part 6 provided on one side of the in-pipe pressure receiving aperture part B; a diaphragm 8 provided to be loosely mounted at the peripheral edge of the opening part; and a guide 10 bonded to the diaphragm and arranged to be connected with one end of the load transfer means 3.

Further, a male pattern 11 is provided at the in-pipe pressure receiving aperture part B and a female pattern 11' is provided at the pressure detecting part A and, with these patterns, a positioning means is formed and the pressure detecting part A is detachably engaged with the in-pipe pressure receiving aperture part B so as to be vertically installed. Furthermore, an engaging means for the pressure detecting part A and the in-pipe pressure receiving aperture part B is formed from a male pattern 12 provided at the load transfer means 3 of the pressure detecting part A and a female pattern 12' provided at the guide 10 of the in-pipe pressure receiving aperture part B, and the pressure detecting part A and the in-pipe pressure receiving aperture part B are connected through the engaging means.

Now, pressure detection operation of the pressure detecting device of the present invention will be described.

In the pressure detecting device of the present invention, when the pressure of fluid flowing through fluid passage 7 fluctuates, the diaphragm 8 physically deforms due to the pressure change. That is, when the pressure of fluid passing through the fluid passage 7 becomes a positive pressure compared to the pressure at the starting time of the measurement, the diaphragm 8 deforms in such a way to expand toward pressure detecting element 1 (X direction in the figure). Also, when the pressure of the fluid passing through the fluid passage becomes a negative pressure compared to the pressure at the starting time of the measurement, the diaphragm 8 deforms toward the fluid passage 7 into a concave shape. The load due to physical deformation of the diaphragm will be transferred to the load transfer means 3 via the guide 10. Thereby, the load transfer means 3 moves in the housing 2 toward either the pressure detecting element 1 (X direction in the figure) or the fluid passage in the opposite direction. The movement of the load transfer means 3 transfers a load to the pressure detecting element 1 in abutment thereto; and as the result, it is made possible to detect the pressure of fluid in the fluid passage 7.

The pressure detecting element used in the present invention is a load converter (load cell) of which general function is to measure only the load applied toward the pressure detecting element itself. There are two types of load cells: one capable of measuring both positive and negative pressures and one capable of measuring only the load in the positive pressure range. In view of the purpose of the present invention, it is desirable to adopt the former type, which can measure the load in both positive and negative pressure ranges. However, this type of load cell suffers from complexity in locating a reference point (zero point) and in the mechanism for measuring pressure in both directions, making the equipment body oversized, and therefore is not suitable for pressure detecting devices such as those of the present invention. Therefore, the present invention adopts a mechanism for measuring both positive and negative pressures by using a load cell capable of measuring the load only in the positive pressure range, which has potential for size reduction, and applying a pre-load toward the load cell at the start time of measurement to make it a reference point for measurement (zero point).

In a conventional pressure detecting device of a diaphragm/load cell type, the load cell directly or indirectly applied a load on the diaphragm, while in the pressure detecting device of present invention, the load applying means 4 applies a load toward the pressure detecting element 1 (toward the load cell) on the diaphragm via the load transfer means 3. Thus, it is made possible to reduce the stress applied to the diaphragm.

Further, the diaphragm 8 is loosely mounted, that is, mounted with its membrane being slackened, at the opening part provided on one side of the in-pipe pressure detecting aperture part. When the diaphragm 8 is stretchedly mounted, that is, mounted with its membrane being stretched, the diaphragm 8 will be constantly subjected to a load for a long period of time when the device is operated for a long period of time, thereby causing a creep deformation of the diaphragm. Therefore, by loosely mounting the diaphragm consisting the pressure detecting device in the present invention, it is made possible to reduce the stress applied to the diaphragm.

In FIG. 1, the configuration of the diaphragm 8 is such that after being loosely mounted at the peripheral edge of the opening part 6 of the base 5, the diaphragm 8 is held between positioning means. When holding the diaphragm 8, it may be held through an O-ring (not shown) between the base 5 and the positioning means. Further, the configuration maybe such that the base 5 is comprised of two parts between which the diaphragm 8 and the O-ring are held. The distance of the space between the opposing positioning means is preferably smaller than the distance of the bottom part of the guide 10 in contact with the diaphragm 8, because even if the pressure detecting part A is suddenly detached from the in-pipe pressure receiving aperture part B, it becomes possible to prevent the diaphragm 8 from being excessively expanded by the pressure applied by fluid thereby protruding further than the position of the positioning means resulting in a breakage of the diaphragm 8.

As so far described, by applying pressure toward the pressure detecting element 1 on the load transfer means 3 connected to the diaphragm 8, and loosely mounting the diaphragm 8, it is made possible to reduce the stress applied on the diaphragm and thus to prevent an irreversible creep deformation of the diaphragm.

The material of the diaphragm 8 used in the present invention is preferably a flexible material because it is required to generate physical variation in response to the pressure fluctuations of fluid. Further, since the material will be in contact with the fluid passing through the fluid passage 7, a material which will not negatively affect the fluid to be measured (principally blood) is desirable. Further, since the diaphragm needs to be prepared by heat treating a planar membrane to form a suitable shape for loose mounting, a material having good workability is preferable. From the reasons described so far, a preferable material for the diaphragm 8 is polyvinyl chloride or the like.

In the pressure detecting device of the present invention, the connection between the load transfer means 3 and the diaphragm 8 is preferably implemented through the guide 10 which has been connected to the diaphragm 8 beforehand. The pressure detecting part A comprising the load transfer means 3 of the pressure detecting device of the present invention may be, for example, part of a mechanical component of an extra corporeal circulation apparatus, and the in-pipe pressure receiving aperture part B comprising the diaphragm 8 maybe, for example, part of a component of an extra corporeal circulation line. Therefore, considering the treatment of the apparatus after use, it is advantageous to separate the extra corporeal circulation line, which is disposable after a single use, from the mechanical part of the extra corporeal circulation apparatus. Further, the connecting part of the load transfer means 3 and the guide 10 are preferably connected through an engaging means provided on each of them. This is because when the both ends are engaged through the engaging means, they are not likely to be detached during usage of the pressure detection device, making it possible to transfer the physical variation of the diaphragm 8 due to the pressure fluctuations in the fluid passage 7 to the load transfer means 3 via the guide 10. Although, in the example shown in FIG. 1, the mechanism of the engaging means is shown as a female pattern engaging means on the guide 10 and a male pattern engaging means on the load transfer means 3, the present invention will not be limited by this embodiment of the connection based on these male and female patterns, and the advantages of the present invention will be successfully achieved even by way of connection means based on magnetic force.

If the connection between the aforementioned load transfer means 3 and the aforementioned guide 10 is based on magnetic force, attaching/detaching operation of the pressure detecting part A and the in-pipe pressure receiving aperture part B will become easier, which is advantageous.

During the use of the pressure detecting device of the present invention, the aforementioned connecting parts are subjected to a load in the detaching direction thereof caused by the physical variation of the diaphragm due to pressure fluctuations in the fluid passage. However, a load which may actually occur is substantially very small, and is not large enough to cause detachment between the aforementioned load transfer means 3 and the aforementioned guide 10 even when the connection is implemented through engagement by a female and a male patterns, or by magnetic force.

Further, when a magnet is placed at the load transfer means and the guide as the aforementioned connecting means based on magnetic force, the configuration may be such that a magnet is provided at each connecting end making both ends attract each other, or such that a magnet is provided at one connecting end and a metal piece etc. is provided at the other end making both connecting ends attract each other. There is no limitation on the way to provide magnets at both ends, and any method will be acceptable.

Furthermore, as the aforementioned connecting means based on magnetic force, one based on an electromagnet is preferable. Since when the connection of both ends is based on an electromagnet, connection and disconnection of both ends will be facilitated by selecting on/off of the current through the electromagnet. The easiness of this connection and disconnection makes it easy to correct the connecting position of both sides.

In order to reduce the stress imposed on the diaphragm, the load transfer means 3 connected thereto via the guide 10 is applied with a pre-load toward the detecting element 1 by means of the load applying means 4. The load applying means 4 is preferably a perfect elastic body which exhibits no elastic hysteresis and of which strain (deformation) will disappear as soon as the outer force is removed.

The aforementioned elastic body is preferably a coiled spring. As shown in FIG. 1, a coiled spring is advantageous in that it is structurally convenient to install the coiled spring surrounding the load transfer means and placing them together in the hollow part of the housing 2 and also in that the detecting range of negative pressure of the pressure detecting device and the spring coefficient can be arbitrarily set by means of the spring coefficient of the coiled spring and the length of the spring.

As for the aforementioned spring coefficient, it is appropriate to set the spring coefficient to be 0.2 to 1.0 N/mm for detecting the fluid pressure within an extra corporeal circulation line used for hemodialysis. Further, it is preferable to set the load to be applied toward the pressure detecting element 1 (toward the load cell) to be in a range of 0.01 Kgf to 10 Kgf. Further, in the case of fluid pressure detection in hemodialysis, it is suitable to set it to be about 1.0 Kgf.

Further, it is possible to achieve an object of the present invention by adopting a mechanism which uses a magnet as the aforementioned load applying means and applies the repulsive force thereof toward the load cell. The aforementioned magnet may be a permanent magnet or an electromagnet. Using an electromagnet makes it relatively easy to set the repulsive force by the magnet, that is, to set the load to be applied, thereby improving the accuracy of the measurement of negative pressure, and therefore is advantageous.

As for the material for the aforementioned coiled spring, the coiled spring may be made of either metal or plastics. Further, if the aforementioned perfect elastic body is a coiled spring, the load transfer means 3 for transferring the physical variation of the diaphragm 8 caused by pressure fluctuations in the fluid passage 7 preferably transfers its load in linear motion in the pressure detecting device of the present invention. For this purpose, it is preferable to configure the entire body of the pressure detecting element A to be a hollow housing 2 within which the load transfer means is slidable. Further, to accurately transfer the physical variation of the diaphragm, in a preferred embodiment, the aforementioned load transfer means 3 is vertically configured with respect to the in-pipe pressure receiving aperture part B. Further, when the aforementioned load transfer means 3 moves due to pressure fluctuations, friction against the housing 2 occurs. Therefore, the aforementioned load transfer means 3 is preferably made of a material with a high sliding property, such as polyacetal.

Further, as shown in FIG. 1, it is preferable that a positioning means for fixing the load transfer means 3 so as to be configured vertically with respect to the in-pipe pressure receiving aperture part B is provided respectively at the housing 2 of the pressure detecting part A having the load transfer means 3 and at the in-pipe pressure receiving aperture part B. In a preferred embodiment, these positioning means are configured so as not only to fix the pressure detecting part A and the pipe inner pressure receiving section B, but also to make them to be detachable. In the example shown in FIG. 1, a male pattern positioning means at the in-pipe pressure receiving aperture part B and a female pattern positioning means at the pressure detecting part A are shown, but the present invention will not be limited by this example.

BEST MODE FOR CARRYING OUT THE INVENTION

EXAMPLE 1

A pressure detecting device of the present invention was fabricated as shown below and its measurement sensitivity was studied.

In-pipe pressure receiving aperture part B
Diaphragm: 22 mm dia.×0.45 mm (polyvinyl chloride)
(In this case, the diaphragm was loosely mounted such that the position of the diaphragm is at a depth of 2 mm toward the fluid passage from the position of the diaphragm at the start time of pressure measurement. And the "slack" of the diaphragm was produced at the peripheral edge of an opening face in one side of the in-pipe pressure receiving aperture part when it was loosely mounted. The width of this "slack" was set to be 1 mm from the peripheral edge of the opening face in one side of the in-pipe pressure receiving aperture part. And the load to be applied toward the pressure detection element was set to be 1.0 Kgf.)
Base part: 44×36×10 mm (W×D×H: Polycarbonate)
Fluid passage: 3.4 mm dia.
Opening part (diaphragm mounting part): 12 mm dia.
O-ring: 20 mm dia.×12 mm dia.×2.4 mm (stainless steel)
Guide: 10 mm dia. (polycarbonate)
Pressure detecting part A
Housing: 20 mm dia.×9 mm dia.×26 mm (polycarbonate)
Load transfer means: 6 mm dia.×25 mm (polyacetal)

Figure 1:
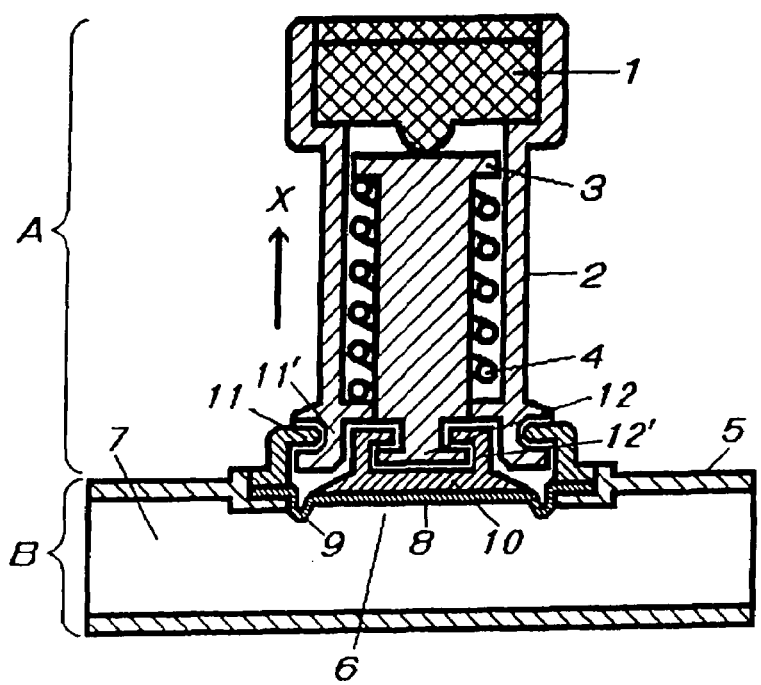
FIG. 1 is a sectional view of the pressure detecting device of the present invention.
Figure 2:
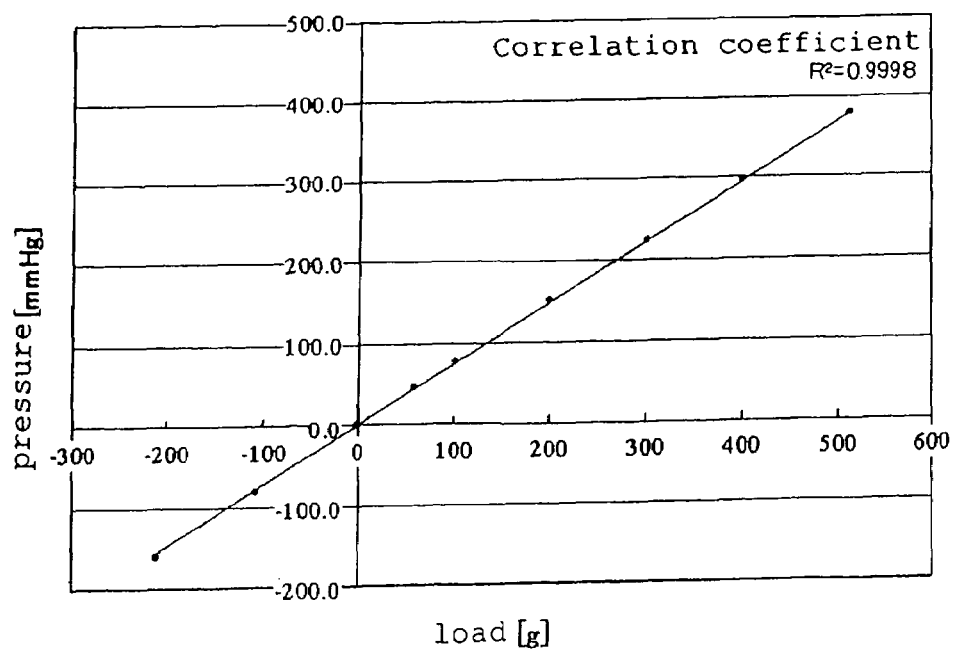
FIG. 2 is a load-pressure calibration curve obtained from the pressure measurements by the pressure detecting device of the present invention.

FIG. 2 illustrates a load-pressure calibration curve to show the result of the study of the measurement sensitivity. As shown in FIG. 2, the load-pressure calibration curve obtained from the measurement data by the pressure detecting device of the present invention showed good linearity (correlation coefficient: 0.999) at least in a range of –150 mm Hg to 400 mm Hg thereby demonstrating that the pressure detecting device of the present invention can measure pressure at a high sensitivity.

EXAMPLE 2

Figure 3:
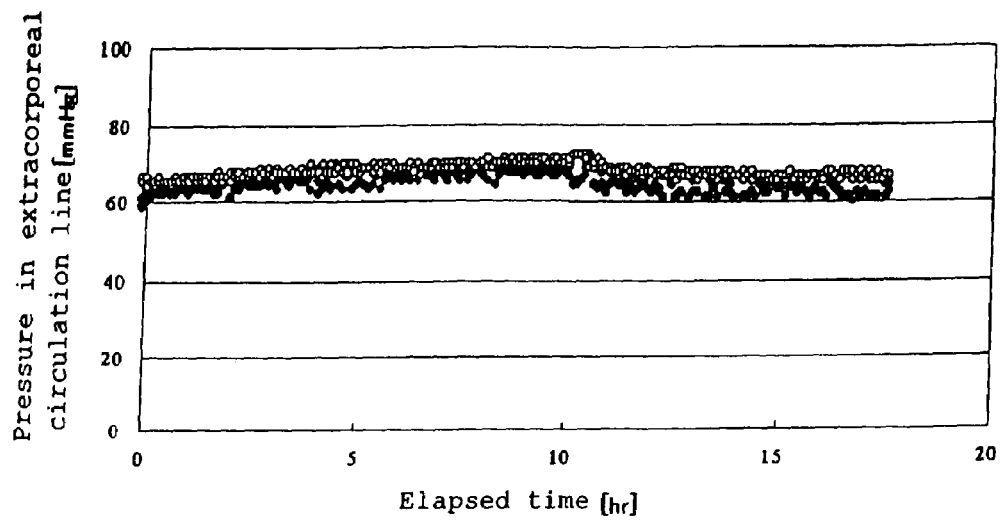
FIG. 3 is a graph obtained from time-varying pressure measurement data by use of the pressure detecting device of the present invention and a drip chamber.

The stability of measurement sensitivity was studied by using the pressure detecting device shown in the above described example 1. The pressure measurements obtained by use of the pressure detecting device installed in a blood line for extra corporeal circulation after a continuous operation of 18 hours were compared with the pressure measurements obtained by use of a conventional drip chamber in terms of the variation with time. Bovine blood (total protein: 6.0 plus or minus 1.0 g/dL, hematocrit: 30 plus and minus 1%) was used as the fluid and the flow rate was 200 mL/min in the experiment. FIG. 3 is a graph to show the temporal variation of both the measurements. As shown in FIG. 3, pressure values measured by the present pressure detecting device stably followed the pressure values measured at a drip chamber for as long as 18 hours, and the differences between both pressure measurements were within a range of 7 mmHg. Further, for comparison with the result to be attained by the best mode for carrying out the present invention, the following comparative example was prepared.

COMPARATIVE EXAMPLE 1

Figure 4:
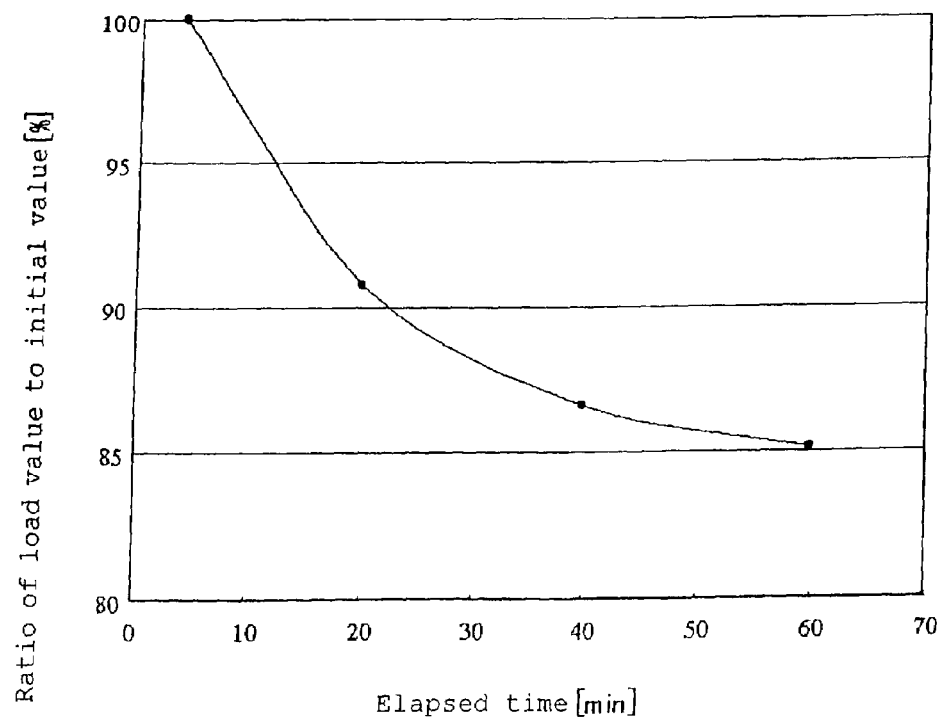
FIG. 4 shows a graph obtained from the time-varying pressure measurement data by a device in which the load applying means is removed from the pressure detecting device of the present invention. Further, in the figures, symbol 1 denotes a pressure detecting element, symbol 2 a housing, symbol 3 a load transfer means, symbol 4 a load applying means, symbol 5 a base, symbol 6 an opening part, symbol 7 a fluid passage, symbol 8 a diaphragm, symbol 9 slack, symbol 10 a guide, symbol 11 a male pattern for forming a positioning means provided at in-pipe pressure receiving aperture part B, symbol 11' a female pattern for forming a positioning means provided at the housing 2 of pressure detecting part A, symbol 12 a male pattern for forming an engaging means for the pressure detecting part A and the in-pipe pressure receiving aperture part B provided at the load transfer means 3 of pressure detecting part A and, symbol 12' a female pattern for forming an engaging means for the pressure detecting part A and the in-pipe pressure receiving aperture part B provided at the guide 10 of the in-pipe pressure receiving aperture part B, symbol A a pressure detecting part, and symbol B an in-pipe pressure receiving aperture part, respectively.

The effect of the coiled spring (load applying means) on the measurement was studied by fabricating a pressure detecting device excluding the coiled spring in the pressure detecting part in the pressure detecting device shown in the above described example 1. FIG. 4 is a graph to show the change of the measured data with respect to the initial value obtained through pressure measurement for an hour while keeping the pressure of fluid constant. As the result, as shown in FIG. 4, the pressure measurements decreased with time indicating that there occurred differences between the pressure values of the fluid and the measured values. This result revealed that in the pressure detecting device of the present invention, with the coiled spring being removed, that is, the diaphragm being subjected to a load, the diaphragm would undergo a creep deformation thereby causing discrepancies between the fluid pressure values and the measured values thus disabling accurate pressure measurement.

The results shown above demonstrated that the pressure detecting device of the present invention, which adopts a method of applying a pre-load toward the pressure detecting element, can measure the pressure in a blood line of extra corporeal circulation at a high accuracy for a long period of time without causing a creep deformation of the diaphragm during measurement.

INDUSTRIAL APPLICABILITY

According to the pressure detecting device of the present invention, which is configured to measure the fluid pressure in a fluid passage via a diaphragm so that the fluid to be measured will not be directly exposed to the air, it is possible to reduce the possibility of line blockage due to blood coagulation and so on. Further, since stress imposed upon the diaphragm is reduced by applying a load on the load transfer means, which is connected to the diaphragm provided in the pressure detecting device, toward the pressure detecting element by use of the load applying means, and further loosely mounting the diaphragm 8, it becomes possible to prevent an irreversible creep deformation of the diaphragm. Thus, it is possible to provide a pressure detecting device which is capable of measuring pressure in a continuous and stable manner for a long period of time.

As so far described, the pressure detecting device of the present invention has advantages not only in enabling safe execution of extra corporeal circulation, but also in facilitating the monitoring during the execution of extra corporeal circulation.

The invention claimed is:

1. A pressure detecting device having: an in-pipe pressure receiving aperture part comprising a fluid passage for transporting fluid and a diaphragm hermetically sealing an opening part provided in one side of the fluid passage; and a pressure detecting part coupled with the in-pipe pressure receiving aperture part through the diaphragm and adapted to detect physical variation of the diaphragm, characterized in that:

the diaphragm is loosely mounted at the opening part; and said pressure detecting part at least comprises a pressure detecting element, a load transmitting means having one end connected with the diaphragm and the other end in contact with said pressure detecting element, and a load applying means for applying a load on said pressure detecting element.

2. The pressure detecting device according to claim 1, characterized in that said load transfer means is connected to the diaphragm via a guide bonded to the diaphragm.

3. The pressure detecting device according to claim 2, characterized in that said load transfer means and the guide are connected by being interlocked with an engaging means provided at each of them respectively.

4. The pressure detecting device according to claim 2, characterized in that said load transfer means and said guide are connected by a connecting means based on magnetic force.

5. The pressure detecting device according to claim 1, characterized in that said load transfer means is an elastic body.

6. The pressure detecting device according to claim 5, characterized in that said elastic body is a coiled spring.

7. The pressure detecting device according to claim 1, characterized in that said load applying means is based on magnetic force.

8. The pressure detecting device according to claim 7, characterized in that said load applying means is an electromagnet.

9. The pressure detecting device according to claim 1, characterized by being configured such that the entire body of said pressure detecting part is a hollow housing within which the load transfer means is vertically movable.

10. The pressure detecting device according to claim 1, characterized in that a positioning means is provided at each of the in-pipe pressure receiving aperture part and the pressure detecting part, and said in-pipe pressure receiving aperture part and said pressure detecting part are detachably connected.

11. A method of pressure detection characterized by comprising:

using a pressure detecting device having: a in-pipe pressure receiving aperture part comprising a fluid passage for transporting fluid and a diaphragm hermetically sealing an opening part provided one side of the fluid passage; and a pressure detecting part coupled with the in-pipe pressure receiving aperture part through the diaphragm and adapted to detect physical variation of the diaphragm, wherein said diaphragm is loosely mounted at said opening part, and said pressure detecting part uses a pressure detecting device comprising at least a pressure detecting device, a load transmitting means having one end connected with the diaphragm and the other end touching the pressure detecting device, and means for loading the pressure detecting device; and detecting the pressure of the fluid transported into the fluid passage of the in-pipe pressure receiving aperture part through a diaphragm loosely mounted at the in-pipe pressure receiving aperture part with a load being applied toward said pressure detecting element.

* * * * *